United States Patent
Lee et al.

(10) Patent No.: US 6,902,746 B2
(45) Date of Patent: Jun. 7, 2005

(54) ORAL PHARMACEUTICAL COMPOSITIONS CONTAINING NON-STEROIDAL ANTI-INFLAMMATORY DRUGS AND METHOD FOR PREPARING THE SAME

(75) Inventors: Fang-Yu Lee, Taichung (TW); Shan-Chiung Chen, Fengyuan (TW); Ping-Kuen Chen, Taichung (TW); Han-Chiang Kuo, Taichung (TW)

(73) Assignee: Yung Shin Pharmaceutical Industrial Co., Ltd., Taichung (TW)

(*) Notice: Subject to any disclaimer, the term of this patent is extended or adjusted under 35 U.S.C. 154(b) by 162 days.

(21) Appl. No.: 10/187,899

(22) Filed: Jul. 3, 2002

(65) Prior Publication Data

US 2004/0009221 A1 Jan. 15, 2004

(51) Int. Cl.[7] .......................... A61K 9/16; A61K 9/20; A61K 9/22; A61K 9/24; A61K 9/48
(52) U.S. Cl. .................. 424/490; 424/451; 424/457; 424/458; 424/464; 424/468; 424/471; 424/472; 424/490; 424/493; 424/494
(58) Field of Search .................. 424/451, 457, 424/458, 464, 468, 471, 472, 489, 490, 493, 494

(56) References Cited

U.S. PATENT DOCUMENTS

| | | | | |
|---|---|---|---|---|
| 5,738,874 A | * | 4/1998 | Conte et al. | 424/472 |
| 5,753,265 A | * | 5/1998 | Bergstrand et al. | 424/474 |
| 6,306,842 B1 | * | 10/2001 | Lai et al. | 514/159 |
| 6,387,410 B1 | * | 5/2002 | Woolfe et al. | 424/489 |
| 6,391,341 B1 | * | 5/2002 | Mendes et al. | 424/489 |
| 2003/0069255 A1 | * | 4/2003 | Plachetka | 514/255.04 |

\* cited by examiner

*Primary Examiner*—Gollamudi S. Kishore
*Assistant Examiner*—S. Tran
(74) *Attorney, Agent, or Firm*—Fei-Fei Chao; Bingham McCutchen LLP

(57) ABSTRACT

The present invention provides oral pharmaceutical compositions for acetic acid class of non-steroidal anti-inflammatory drug (NSAID), particularly ketorolac. The pharmaceutical composition contains a core, a drug layer (which comprises the drug, a binder, and a disintegrant), a protecting layer, and an enteric coating layer. The oral pharmaceutical compositons are particularly useful for treating patients with moderate to acute pain. The present invention also provides a method for making the pharmaceutical compositions and a method for using the pharmaceutical compositions.

16 Claims, 1 Drawing Sheet

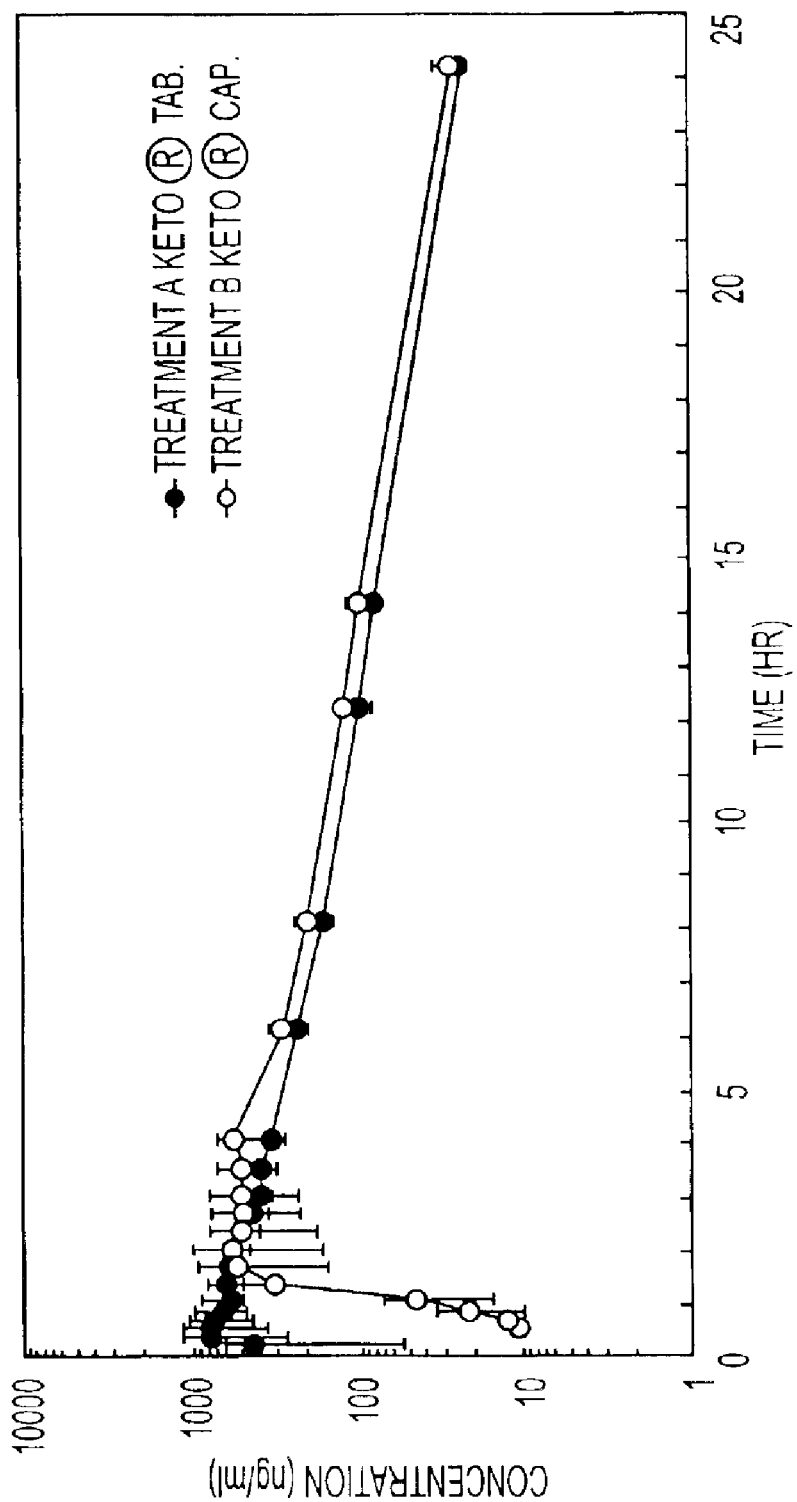

ORAL PHARMACEUTICAL COMPOSITIONS CONTAINING NON-STEROIDAL ANTI-INFLAMMATORY DRUGS AND METHOD FOR PREPARING THE SAME

FIELD OF THE INVENTION

The present invention relates to oral pharmaceutical compositions for acetic acid class of non-steroidal anti-inflammatory drugs (NSAIDs), particularly ketorolac and the pharmaceutically acceptable salt form of ketorolac. The preferred pharmaceutically acceptable salt form of ketorolac is ketorolac tromethamine. The pharmaceutical compositions of the present invention are particularly effective in providing moderate to acute pain relief. The pharmaceutical compositions comprise an inert core, a drug layer, a protecting layer and an enteric coating layer. The drug layer includes an NSAID, a binder, and a disintegrant. The present invention also relates to a method for preparing the same.

BACKGROUND OF THE INVENTION

Post-surgery pain control is one of the most difficult problems faced by healthcare professionals. At the present time, there are roughly two frequently-used analgesics: the anesthetic analgesics (opioids), and the non-steroidal anti-inflammatory drugs (NSAIDs).

The opioid-type of analgesics acts on the central nervous system and provides relief for moderate to severe pain. Though in the management of severe pains, opioids are very potent pain relievers, they have the history of developing tolerance, drug abuse, physical and mental dependency, withdrawal symptoms and adverse effects, which make their uses controversial.

Nonsteroidal anti-inflammatory drugs ("NSAIDs"), on the other hand, are widely used for treatment of minor discomfort and illness and many disease conditions such as cold, aches and pains, mild fever, osteoarthritis, rheumatoid arthritis, acute or severe pain, etc. At the present time, NSAIDs are among the most prescribed drugs in the world, with annual sales exceeding $6 billion.

NSAIDs are a family of drugs that generally have analgesic, antipyretic, and anti-inflammatory activities. These activities derive from a common mechanism: the inhibition of cyclooxygenase, which is the critical enzyme for biosynthesis of prostaglandins, prostacyclin, and thromboxanes. Because prostaglandins are released in response to inflammatory stimuli, which in turn result in inflammatory responses (e.g., redness, pain, heat and swelling of tissue), inhibition of prostaglandins by NSAIDs results in analgesia. In the central nervous system, NSAIDs are antihyperalgesic through a direct action on the spinal cord.

One NSAID, ketorolac, which belongs to the acetic acid class of NSAIDs, are comparable to opioids in terms of providing pain relief. Its salt form, ketorolac tromethamine is a highly potent non-narcotic analgesic with a moderate anti-inflammatory activity. It is efficacious in treating pain arising from a broad spectrum of causes, such as postoperative pain, cancer pain, migraine headache and pain from dental extractions. (Suayib et al. *Acta Oncologica* 36: 231–232, (1997); and DeAndrade & Maslanka, *Orthopedics*, 17: 157–166, (1994)).

Ketorolac has less adverse side effects than narcotic drugs, does not have the side effects associated with opioids, and has not been shown to have physiological addictive potential. This drug appears to be an excellent choice for treating moderate to acute pain.

Ketorolac is a derivative of pyrrolizine carboxylic acid and is structurally related to tolmetin and zomepirac. The most commonly used form of ketorolac is ketorolac tromethamine. The chemical name for ketorolac tromethamine is (±)-5-benzoyl-2,3-dihydro-1H-pyrrolizine-1-carboxylic acid 2-amino-2-(hydroxymethyl)-1,3-propanediol. Its chemical structure is as follows:

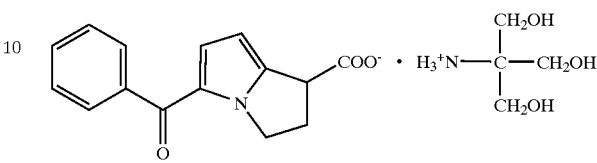

Ketorolac tromethamine has a pKa of 3.5 and an n-octanol/water partition coefficient of 0.26. The molecular weight of ketorolac tromethamine is 376.41.

Although NSAIDs are highly effective, their use in oral administration has been associated with significant adverse effects, most notably those involving the gastrointestinal (GI) system.

There are two major ulcerogenic effects of NSAIDs: (1) topical irritant effects on the epithelium of the GI tract, and (2) suppression of GI prostaglandin synthesis. In recent years, there have been numerous attempts to design and develop new NSAIDs that reduce damage to the GI tract. These efforts, however, have largely been unsuccessful. For example, enteric coating or slow-release formulations designed to reduce the topical irritant properties of NSAIDs have been shown to be ineffective in terms of reducing the incidence of clinically significant side effects, including perforation and bleeding. (Wallace and Chin, *Drugs of Today*, 33:115–122 (1997)).

Others have suggested combining the use of NSAIDs with other drugs which have the effect of eliminating or resisting GI side effects caused by NSAIDs (the so-called "prophylactic therapy"). For example, misoprostol can be used to make up for the prostaglandin deficiency caused by NSAIDs. Drugs that suppress the secretion of stomach acid, such as $H_2$-antagonists or proton pump inhibitors, can also be used.

In the invention to be presented in the following sections, novel oral pharmaceutical compositions containing NSAIDs, particularly ketorolac tromethamine, are described. These pharmaceutical compositions contain an inert core, a drug layer, a protecting layer, and an enteric coating layer. The protecting layer protects the drugs from light and humidity. The enteric coating layer protects patients from ulcerogenic effects.

SUMMARY OF THE INVENTION

The present invention provides pharmaceutical compositions which are characterized for their containing: (1) a core; (2) a drug layer (which contains an effective amount of an acetic acid class of non-steroidal anti-inflammatory drug (NSAID), a binder, and a disintegrant; (3) a protecting layer; and (4) an enteric coating layer. Preferably, the core is about 25–40% by weight, the drug layer is about 5–15% by weight, the protecting layer is about 5–15% by weight, and the enteric coating layer is about 40–55% by weight of the total pharmaceutical composition. The preferable amount of the acetic acid class of NSAID is about 1–15% by weight of the total pharmaceutical composition.

Examples of the acetic acid class of NSAID include, but are not limited to, ketorolac and diclofenac. The preferred drug used in the present invention is ketorolac, particularly the salt form of ketorolac, ketorolac tromethamine.

The core of the pharmaceutical compositions is either obtained from commercially available sources or prepared in-house. Examples of the core materials include, but are not limited to, at least one of the following compounds: sucrose, starch, talc, and microcrystalline cellulose.

In addition to the acetic acid class of NSAID, the drug layer contains a binder and a disintegrant. The binder is about 0.1–7% by weight of the total pharmaceutical composition. The disintegrant is about 3–15% by weight of the total pharmaceutical composition.

Examples of the binder include, but are not limited to, at least one of the following polymers: hydroxypropyl methylcellulose (HPMC), hydroxypropyl cellulose (HPC), polyvinyl pyrrolidone (PVP) and hydroxy methylcellulose (HMC). The preferred binder is PVP K-30.

Examples of the disintegrant include, but are not limited to, at least one of the following compounds: starch and sodium starch glycolate.

Optionally, a diluent is added to the drug layer. Examples of the diluent include, but are not limited to, at least one of the following compounds: lactose, sucrose, and mannitose.

The protecting layer comprises at least one of the following polymers: hydroxypropyl methylcellulose (HPMC), hydroxypropyl cellulose (HPC), and Hydroxymethylcellulose (HMC). The preferred polymer is hydroxypropyl methylcellulose (HPMC).

In addition to the polymer, optionally, a plasticizer can be added to the protecting layer. Examples of the plasticizer include, but are not limited to, at least one of the following compounds: dimethyl phthalate, diethyl phthalate, triacetin, triethyl citrate, and polyethylene glycol (PEG). The preferred plasticizer is PEG, particularly PEG 6000.

Also optionally, an opaque agent, titanium oxide ($TiO_2$) can be added to the protecting layer. The opaque agent can prevent the drug from discoloration.

The enteric coating layer comprises at least one polymer which is selected from the group consisting of hydroxypropylmethylcellulose phthalate (HPMCP), cellulose acetate phthalate (CAP), Eudragit L, and Eudragit S; and at least one plasticizer which is selected from the group consisting of dimethyl phthalate, diethyl phthalate, triacetin, triethyl citrate, and polyethylene glycol (PEG).

The present invention also provides a method for preparing the pharmaceutical compositions. The method includes the following steps: (1) obtaining a core either by purchasing from bulk drug companies or preparing in house; (2) spraying a drug layer onto the core to form a drug-containing core; (3) spraying a protecting layer onto the drug-containing core to form a protecting layer-containing drug granule; and (4) spraying an enteric coating layer onto the protecting layer-containing drug granule to form the pharmaceutical composition. A detailed process of making the core, the drug layer, the protecting layer and the enteric coating layer is provided in the "Detailed Description of The Invention" Section, infra.

Finally, the present invention provides a method for using the pharmaceutical compositions to treat patients with pain, which includes giving patients the effective dosage of the pharmaceutical composition orally.

BRIEF DESCRIPTION OF THE DRAWING

FIG. 1 shows the plasma concentrations of ketorolac (ng/mL) after orally administered the commercially available Keto® tablet (Treatment A; ●, solid circle) (manufactured by Yung-Shin Pharma Indust. Ltd., Taiwan) and the Keto® capsule prepared as described in Example 7 (Treatment B; ○, open circle). Value=Mean ±S.D.

DETAILED DESCRIPTION OF THE INVENTION

The non-steroidal anti-inflammatory drugs (NSAIDs) have analgesic, antipyretic and anti-inflammatory activities. At the present time, there are six NSAID groups: which are, acetylsalicylic acid, propionic acid, acetic acid, fenamate (anthranillic acid), nonacidic, and oxicam groups.

One agent in the acetic acid group, ketorolac, has a potent analgesic activity at the opioid level and is indicated for management of moderately severe acute pain. Contrary to opioids, ketorolac is a relatively safe and effective drug for use in pain relieves. It does not bind to the M.K. and δ opioid receptors and does not affect central nervous system and display narcotic-like action. Ketorolac is also superior to other agents in the same class, probably due to its ability to induce the release of endogenous opioids and antagonize N-methyl-D-aspartate (NMDA) receptors and gama-aminobutyric acid (GABA) interneurons. It selectively inhibits cyclooxygenase and blocks the formation of inflammatory pain factors.

The present invention provides novel pharmaceutical compositions of non-anesthetic analgesic anti-inflammatory properties for management of acute pain. In particular, the pharmaceutical compositions of the present invention contain ketorolac, especially ketorolac tromethamine, as the active pharmaceutical ingredient.

Ketorolac tromethamine is a chiral drug which can be separated into two racemic structures, i.e., [−]S and [+]R ketorolac forms. The biological activity of ketorolac is associated with the S-form. The term "ketorolac" as used herein refers to S-form, R-form, or a racemic mixture of ketorolac. The racemic mixture of the [−]S and [+]R isomers have been used commercially in oral, ophthalmic, intravenous and intramuscular pharmaceutical products.

Ketorolac tromethamine possesses excellent water solubility. It is easily dissolved in methanol; slightly soluble in ethanol, anhydrous ethanol, and tetrahydrofuran; and insoluble in acetone, dichloromethane, toluene, ethyl acetate, dioxane, hexane, butyl alcohol and acetonitrile. Ketorolac tromethamine has a melting point at 162° C. followed by immediate decomposition. The white to off-white crystalline substance of ketorolac tromethamine is susceptible to discoloration under exposure to light and moisture.

The pharmaceutical compositions of present invention include (1) a core; (2) a drug layer; (3) a protecting layer; and (4) an enteric coating layer. The core is made of inert or neutral materials such as sucrose, starch, or microcrystalline cellulose. Ketorolac tromethamine is included in the drug layer, which has been sprayed onto the core. The formulated into spheres which were coated with protective layer and enteric coating to provide protection against light and moisture as well as enhancing its absorption once it reaches the small intestine.

According to Physician's Desk Reference (56th Ed.), after oral administration of 10 mg of the ketorolac tromethamine formulations of the present invention on empty stomach, ketorolac tromethamine is completely absorbed (more than 95%). The absorption is not affected by the presence of antacids. The mean maximum plasma concentration is reached at about 30 to 60 minutes. Once in the circulation, ketorolac tromethamine disintegrates under the physiological pH into the anion form, in which about 99% are bound to plasma proteins. The mean volume of distribution at steady state is 0.11 L/kg. The mean volume of distribution during the elimination phase is 0.17–0.25 L/kg. The mean elimination half-live is 5.3 hours.

The plasma concentration-time profile can be described by a two- or three-compartmental model. About 91% of the administered drug were excreted in the urine in its original form within 48 hours, in which about 75% were eliminated within the first 7 hours in the urine. About 6% of the administered drug, in its original form, were found in the feces.

Ketorolac tromethamine is primarily metabolized in the liver. Most of the ketorolac metabolites conjugated with glucuronic acid to form inactive substances and excreted out of the body. Among the ketorolac metabolites, p-hydroxyketorolac is primarily excreted in the urine. This hydroxyl metabolite has very weak pharmacological activity. According to animal studies, p-hydroxyketorolac has less than $1/100$ of the analgesic effect of ketorolac tromethamine and less than $1/5$ of the anti-inflammatory effect of ketorolac tromethamine. Based upon the results of in vitro platelet aggregation study, the anti-platelet aggregation activity of p-hydroxyketorolac is $1/25$ of that of ketorolac tromethamine. When administered to elderly patients or patients with renal or liver impairment, their plasma half-lives markedly prolonged and total clearance decreased. The effects were less obvious in patients with liver insufficiency.

The present invention relates to the oral pharmaceutical compositions of ketorolac tromethamine. The pharmaceutical compositions are characterized as comprising, from the inner: a core, a drug layer, a protective layer and an enteric coating.

The ingredients used in the pharmaceutical compositions of the present invention can be generally categorized into the active ingredient, disintegrants, binders, protecting layer ingredients, enteric coating ingredients, plasticizers, opaque agents and solvents. Ketorolac tromethamine is the active ingredient.

Examples of the disintegrants include, but are not limited to, starch, lactose, sucrose and mannitose. Starch and its derivatives are the preferred disintegrants.

(A) The Core:

The cores are made of rounded or spherical neutral, edible particles. The cores can be made in-house using a fluidized bed granulator and dryer (i.e., the Glatt machine), or using standard edible cores purchased from a bulk drug manufacturer.

Usually, there are three kinds of cores that can be purchased:
1. Granulated cores of 100% refined white sugar, or
2. Granulated cores of refined white sugar plus starch, or
3. Granulated cores of microcrystalline cellulose.

The sphericizing materials for the core include certain types of excipients which are capable of forming spherical granules during the granulation process. Non-limiting examples of such filler materials are sucrose, starch, talc, and microcrystalline cellulose.

(b) The Drug Layer:

The drug layer contains at least an NSAID, a binder and a disintegrant.

Examples of NSAID include compounds of the acetic acid class of NSAID, particularly ketorolac and diclofenac. The preferred NSAID is ketorolac, especially ketorolac tromethamine. The amount of NSAID included in the pharmaceutical compositions of the present invention is in the range of about 1–15% by weight of the total pharmaceutical composition, and most preferably in the range of 2–8% by weight.

The amount of binder used in the pharmaceutical compositions of the present invention is preferably in the range of about 0.1–7% by weight of the total pharmaceutical composition, and most preferably in the range of 0.1–1% by weight.

Examples of the binders include, but are not limited to, polyvinyl pyrrolidone (PVP), hydroxypropyl cellulose (HPC), and hydroxypropyl methyl cellulose (HPMC). PVP is the preferred binder. PVP is commonly characterized by the so-called "K-value," which is a useful measure of the polymeric composition's viscosity. PVP can be purchased from Tokyo Chemical Industry Co., Ltd. under the trade name of PVP K15, PVP K30, PVP K60, and PVP K90. The most preferable PVP to be used as a dry binder for ketorolac tromethamine is PVP K30, which has an average molecular weight of 40,000. PVP can be used in either wet or dry state.

The amount of disintegrant used in the pharmaceutical compositions of the present invention is preferably in the range of 1–15% by weight of the total pharmaceutical composition, and most preferably in the range of 3–8% by weight.

Examples of the disintegrant include, but are not limited to, starch and sodium starch glycolate. Optionally a diluent is added to the drug layer. Examples of the diluent include sucrose, lactose and mannitose.

(c) The Protecting Layer:

The polymer used in the protecting layer include, without limitation, the following:
1. HPMC (hydroxypropyl methylcellulose);
2. HPC (hydroxypropyl cellulose); and/or
3. HMC (Hydroxymethylcellulose).

HPMC is the preferred polymer used in the protecting layer.

The solvent used for producing the protecting layer include, without limitation, acetone, alcohol, isopropyl alcohol and methylene chloride, or their mixtures with water.

Optionally, the protecting layer may contain one or more plasticizers to provide stability and ease of manufacturing.

The plasticizers used in the protecting layer may include the following:
1. Dimethyl phthalate;
2. Diethyl phthalate;
3. Triacetin;
4. Triethyl citrate; and/or
5. Polyethylene glycol (PEG).

The preferred plasticizer is PEG, and most preferably PEG 6000. PEG is a generic name for mixtures of condensation polymers of ethylene oxide and water, represented by the general formula of $H(OCH_2CH_2)_n\,OH$, in which n is greater than or equal to 4. The term is used in combination with a numeric suffix which indicates the approximate average molecular weight. The n of PEG 6000 varies from 158 to 204.

Also optionally, an opaque agent, such as titanium dioxide ($TiO_2$), can be added to the protecting layer. The opaque agent is particularly useful in preventing discoloration of the drug due to exposure to light.

(d) Enteric Coating Layer:

At least two kinds of materials are required to form an enteric coating. They are: a polymer and a plasticizer. The polymers for forming the enteric coating layer include, without limitation, the following:

1. Eudragit L (methacrylic acid-carbomethoxyl methacrylic acid copolymer L);
2. Eudragit S (methacrylic acid-carbomethoxyl methacrylic acid copolymer S);
3. HPMCP (hydroxypropyl methylcellulose phthalate); and/or
4. CAP (cellulose acetate phthalate).

Eudragit® series, which include Eudragit®-E, L, S, RL, RS, NE, are commercially available and sold by Rohm & Haas Company. They are polymethacrylic acid-methacrylic acid copolymers. The preferred Eudragit® polymer series to be used in the present invention include Eudragit®-L and S series. The most preferred Eudragit® is Eudragit L30D.

The plasticizer used for making the enteric coating include, without limitation, the following:

1. Dimethyl phthalate;
2. Diethyl phthalate,
3. Triacetin,
4. Triethyl citrate,
5. Polyethylene glycol (PEG).

As in the protecting layer, PEG, particularly PEG 6000, is the preferred plasticizer.

The organic solvents used for forming the enteric coating include, without limitation, acetone, alcohol, isopropyl alcohol, methylene chloride, or their mixture with water.

The following example is illustrative, but not limiting the scope of the present invention. Reasonable variations, such as those occur to reasonable artisan, can be made herein without departing from the scope of the present invention.

EXAMPLE 1

Preparation of the Pharmaceutical Composition of the Present Invention

Materials:

The pharmaceutical composition contains the following ingredients:

| Core | | 1070.4 g | |
|---|---|---|---|
| Drug layer | Ketorolac tromethamine | 129.6 | g |
| | Lactose | 115.2 | g |
| | PVP K-30 | 9.6 | g |
| | Alcohol | 96 | mL |
| | Purified water | 96 | mL |
| Protecting layer | HPMC | 96 | g |
| | PEG 6000 | 19.2 | g |
| | Titanium dioxide | 19.2 | g |
| | Purified water | 1368 | mL |
| Enteric-coating | Eudragit L30D | 1280 | g |
| | Triethyl citrate | 76.8 | g |

Methods:

(1) Core (a) PVP K-30 (40 g) was mixed with 300 mL of isopropyl alcohol, stirred until the PVP K-30 was completely dissolved. Then, purified water (200 mL) was added to the dissolved PVP K-30, stirred until complete dissolution to form a binder solution.

(b) Starch (800 g) and talc (900 g) were uniformly mixed to form a disintegrant mixture.

(c) Sucrose (400 g) was placed in the fluidized granulator (the Glatt or Huttlin machine) where the binder solution was sprayed onto the sucrose to form sucrose-binder particles. At the same time, the disintegrant mixture of (b) was added to the sucrose-binder particles.

(e) The resulting spheres were dried, which formed the neutral or insert cores.

(2) Drug Layer (a) Purified water (96 ml) was added to PVP K-30 (9.6 g), stirred until complete dissolution. Then, 96 ml of ethanol was added to and mixed with the dissolved PVP K-30 solution until a homogenous binder solution was formed.

(b) Ketorolac tromethamine (129.6 g) and lactose (115.2 g) were mixed and consecutively passed through a 150-mesh sieve once and a 40-mesh sieve twice to produce a drug-disintegrant mixture.

(c) The cores from the above mentioned (1) were placed in the granulator and sprayed with the binder solution of (a). At the same time, the drug-disintegrant mixture (b) was added.

(d) The resultant spheres were dried and formed the drug layer-containing spheres.

(3) Protecting Layer (a) HPMC (96 g) and purified water (1368 ml) were mixed and stirred while at the same time, PEG 6000 was added. The solution was stirred until both HPMC and PEG 6000 were dissolved.

(b) Titanium dioxide was passed through a 150-mesh sieve once.

(c) The solution of (a) and $TiO_2$ of (b) were uniformly mixed.

(d) The drug layer-containing spheres were placed in the granulator. The mixture of (c) was sprayed onto the drug layer-containing spheres (c).

(e) The resultant spheres of (d) were dried and formed the spheres containing the protecting layer.

(4) Enteric-coating (a) Eudragit L30D and triethyl citrate were uniformly mixed to form the enteric coating mixture.

(b) The spheres with the protecting layer from (3) were placed in the granulator where the enteric-coating mixture of (a) was uniformly sprayed onto.

(c) The resultant spheres of (b) were dried to form the pharmaceutical composition of Example 1.

EXAMPLE 2

Preparation of the Pharmaceutical Composition of the Present Invention

Materials:

The pharmaceutical composition of Example 2 contained the following ingredients:

| Core | | 1043.52 | g |
|---|---|---|---|
| Drug layer | Ketorolac tromethamine | 129.6 | g |
| | Starch | 132.48 | g |
| | PVP K-30 | 9.6 | g |
| | Alcohol | 96 | mL |
| | Purified water | 96 | mL |
| Protecting layer | HPMC | 115.2 | g |
| | PEG 6000 | 23.04 | g |
| | Titanium dioxide | 23.04 | g |
| | Purified water | 1368 | mL |
| Enteric-coating | Eudragit L30D | 1280 | g |
| | Triethyl citrate | 76.8 | g |

Method:

The preparation of the core, drug-layer, protecting layer and enteric-coating and operating procedures was in accordance with those described in Example 1, super.

EXAMPLE 3

Preparation of the Pharmaceutical Composition of the Present Invention

Materials:

The pharmaceutical composition of Example 3 contained the following ingredients:

| Core | | 939.6 g | |
|---|---|---|---|
| Drug layer | Ketorolac tromethamine | 126 | g |
| | Starch | 132.48 | g |
| | PVP K-30 | 9.6 | g |
| | Alcohol | 96 | mL |
| | Purified water | 96 | mL |
| Protecting layer | HPMC | 192 | g |
| | PEG 6000 | 38.4 | g |
| | Titanium dioxide | 38.4 | g |
| | Purified water | 1920 | mL |
| Enteric-coating | Eudragit L30D | 1280 | g |
| | Triethyl citrate | 76.8 | g |

Method:

The preparation of the core, drug-layer, protecting layer and enteric-coating and operating procedures was in accordance with those described in Example 1, super.

EXAMPLE 4

Preparation of the Pharmaceutical Composition of the Present Invention

Materials:

The pharmaceutical composition of Example 4 contained the following ingredients:

| Core | | 1090.5 g | |
|---|---|---|---|
| Drug layer | Ketorolac tromethamine | 157.5 | g |
| | Starch | 165.6 | g |
| | PVP K-30 | 12 | g |
| | Alcohol | 120 | mL |
| | Purified water | 120 | mL |
| Protecting layer | HPMC | 240 | g |
| | PEG 6000 | 48 | g |
| | Titanium dioxide | 48 | g |
| | Purified water | 2400 | mL |
| Enteric-coating | Eudragit L30D | 2000 | g |
| | Triethyl citrate | 60 | g |

Method:

The preparation of the core, drug-layer, protecting layer and enteric-coating and operating procedures was in accordance with those as described in Example 1, super.

EXAMPLE 5

Preparation of the Pharmaceutical Composition of the Present Invention

Materials:

The pharmaceutical composition of Example 5 contained the following ingredients:

| Core | | 1217.7 g | |
|---|---|---|---|
| Drug layer | Ketorolac tromethamine | 157.5 | g |
| | Starch | 165.6 | g |
| | PVP K-30 | 12 | g |
| | Alcohol | 120 | mL |
| | Purified water | 120 | mL |
| Protecting layer | HPMC | 288 | g |
| | PEG 6000 | 57.6 | g |
| | Titanium dioxide | 48 | g |
| | Purified water | 3201 | mL |
| Enteric-coating | Eudragit L30D | 1440 | g |
| | Triethyl citrate | 43.2 | g |

Method:

The preparation of the core, drug-layer, protecting layer and enteric-coating and operating procedures was in accordance with those as described in Example 1, super.

EXAMPLE 6

Preparation of the Pharmaceutical Composition of the Present Invention

Materials:

The pharmaceutical composition of the present invention was prepared as follows:

| Core | | 1212.9 g | |
|---|---|---|---|
| Drug layer | Ketorolac tromethamine | 157.5 | g |
| | Starch | 165.6 | g |
| | PVP K-30 | 12 | g |
| | Alcohol | 120 | mL |
| | Purified water | 120 | mL |
| Protecting layer | HPMC | 336 | g |
| | PEG 6000 | 67.2 | g |
| | Titanium dioxide | 48 | g |
| | Purified water | 3750 | mL |
| Enteric-coating | Eudragit L30D | 1280 | g |
| | Triethyl citrate | 38.4 | g |

Method:

The preparation of the core, drug-layer, protecting layer and enteric-coating and operating procedures was in accordance with those as described in Example 1, super.

EXAMPLE 7

Preparation of the Pharmaceutical Composition of the Present Invention

Materials:

The pharmaceutical composition of Example 7 contained the following ingredients:

| Core | | 1196.1 g | |
|---|---|---|---|
| Drug layer | Ketorolac tromethamine | 157.5 | g |
| | Starch | 165.6 | g |
| | PVP K-30 | 12 | g |
| | Alcohol | 120 | mL |
| | Purified water | 120 | mL |
| Protecting layer | HPMC | 240 | g |
| | PEG 6000 | 48 | g |
| | Titanium dioxide | 48 | g |
| | Purified water | 2400 | mL |
| Enteric-coating | Eudragit L30D | 1680 | g |
| | Triethyl citrate | 50.4 | g |

Method:

The preparation of the core, drug-layer, protecting layer and enteric-coating and operating procedures was in accordance with those as described in Example 1, super.

Results of Examples 1–7

The pharmaceutical compositions of EXAMPLES 1–7 are summarized in Table 2:

TABLE 1

Pharmaceutical Compositions of Examples 1–7

| Component | 1 | 2 | 3 | 4 | 5 | 6 | 7 |
|---|---|---|---|---|---|---|---|
| Core | 1070.4 g | 1043.52 g | 939.6 g | 1090.5 g | 1217.7 g | 1212.9 g | 1196.1 g |
| Drug layer | | | | | | | |
| Ketorolac tromethamine | 129.6 g | 129.6 g | 126 g | 157.5 g | 157.5 g | 157.5 g | 157.5 g |
| Lactose | 115.2 g | — | — | — | — | — | — |
| Starch | — | 132.48 g | 132.48 g | 165.6 g | 165.6 g | 165.6 g | 165.6 g |
| PVP K-30 | 9.6 g | 9.6 g | 9.6 g | 12 g | 12 g | 12 g | 12 g |
| Alcohol | 96 mL | 96 mL | 96 mL | 120 mL | 120 mL | 120 mL | 120 mL |
| Purified water | 96 mL | 96 mL | 96 mL | 120 mL | 120 mL | 120 mL | 120 mL |
| Protecting Layer | | | | | | | |
| HPMC | 96 g | 115.2 g | 192 g | 240 g | 288 g | 336 g | 240 g |
| PEG 6000 | 19.2 g | 23.04 g | 38.4 g | 48 g | 57.6 g | 67.2 g | 48 g |
| Titanium dioxide | 19.2 g | 23.04 g | 38.4 g | 48 g | 48 g | 48 g | 48 g |
| Purified water | 1368 mL | 1368 mL | 1920 mL | 2400 mL | 3201 mL | 3750 mL | 2400 mL |
| Enteric-coating | | | | | | | |
| Eudragit L30D | 1280 g | 1280 g | 1280 g | 2000 g | 1440 g | 1280 g | 1680 g |
| Triethyl citrate | 76.8 g | 76.8 g | 76.8 g | 60 g | 43.2 g | 38.4 g | 50.4 g |

The USP XXII dissolution test was carried out on the ketorolac tromethamine oral spheres prepared as described in the examples. The results are summarized in Table 2 as follows:

TABLE 2

% Dissolution of Ketorolac Tromethamine Oral Dosage Forms in Examples 1–7

| | Duration and pH | |
|---|---|---|
| Example | 0.1 N HCl (120 min) 100 rpm | pH 6.8 (30 min) 100 rpm |
| 1 | 8.5% | 86.7% |
| 2 | 5.3% | 93.3% |
| 3 | 0% | 99.6% |
| 4 | 0.25% | 90.95% |
| 5 | 0% | 95.7% |
| 6 | 0% | 100.5% |
| 7 | 0.86% | 107.26% |

Example 7 of the ketorolac tromethamine oral dosage form was further analyzed in accordance with the USP XXII dissolution test requirement using various media and rotation speeds. The results are summarized in Table 3 as follows:

TABLE 3

% Dissolution of Ketorolac Tromethamine Oral Dosage Form of Example 7

| | Duration and pH | | |
|---|---|---|---|
| Rotation speed | 0.1 N HCl (120 min) | pH 4.5 (120 min) | pH 6.8 (120 min) |
| 50 rpm | 0.62% | 3.87% | 103.11% |
| 75 rpm | 1.14% | 4.56% | 105.93% |
| 100 rpm | 0.86% | 4.28% | 107.26% |

Tables 4A and 4B shows the comparative studies of pharmacokinetic results (the time course of plasma concentrations) of the commercially available ketorolac tromethamine tablets (manufactured by Yung-Shin Pharma Indust. Ltd., Taiwan) (Table 4A—Treatment A) and the ketorolac tromethamine tablets as described in Example 7 (Table 4B—Treatment B) in healthy human volunteers. Twelve (12) healthy human subjects (i.e., 1-A to 12-A in Treatment A and 1-B to 12-B in Treatment B) were tested and their mean plasma drug concentrations were calculated, respectively. The mean plasma concentration-time profile of Treatment A (●, solid circle) and Treatment B (○, open circle) is also shown in FIG. 1.

TABLE 4A

Mean Plasma Concentrations-Time Profile of Commercially Available Ketorolac Tablets

| Time (hr) | 1-A | 2-A | 3-A | 4-A | 5-A | 6-A | 7-A | 8-A | 9-A | 10-A | 11-A | 12-A | Mean | SD |
|---|---|---|---|---|---|---|---|---|---|---|---|---|---|---|
| 0 | 0 | 0 | 0 | 0 | 0 | 0 | 0 | 0 | 0 | 0 | 0 | 0 | 0 | 0 |
| 0.167 | 1101 | * | 347 | 227 | 969 | 452 | 37.1 | 86.1 | 26.4 | 411 | 561 | * | 422 | 371 |
| 0.33 | 1135 | 61.3 | 1061 | 662 | 1048 | 1116 | 122 | 334 | 811 | 1177 | 1097 | 49.6 | 723 | 458 |
| 0.5 | 934 | 252 | 1073 | 881 | 883 | 1112 | 155 | 521 | 1008 | 1043 | 990 | 93.6 | 745 | 381 |
| 0.67 | 784 | 482 | 996 | 964 | 739 | 1009 | 174 | 591 | 1013 | 981 | 916 | 182 | 736 | 312 |
| 0.83 | 701 | 614 | 921 | 1032 | 706 | 951 | 198 | 594 | 949 | 847 | 816 | 365 | 725 | 251 |
| 1 | 646 | 637 | 810 | 916 | 665 | 841 | 249 | 592 | 875 | 784 | 781 | 463 | 688 | 191 |
| 1.33 | 545 | 593 | 699 | 965 | 544 | 719 | 373 | 590 | 809 | 662 | 697 | 521 | 643 | 153 |

TABLE 4A-continued

Mean Plasma Concentrations-Time Profile of
Commercially Available Ketorolac Tablets

| Time (hr) | 1-A | 2-A | 3-A | 4-A | 5-A | 6-A | 7-A | 8-A | 9-A | 10-A | 11-A | 12-A | Mean | SD |
|---|---|---|---|---|---|---|---|---|---|---|---|---|---|---|
| 1.67 | 484 | 584 | 600 | 835 | 461 | 640 | 576 | 527 | 711 | 598 | 610 | 448 | 590 | 109 |
| 2 | 423 | 526 | 550 | 760 | 428 | 559 | 669 | 517 | 636 | 545 | 541 | 392 | 546 | 106 |
| 2.33 | 381 | 493 | 480 | 676 | 377 | 489 | 570 | 494 | 582 | 473 | 471 | 343 | 486 | 94 |
| 2.67 | 333 | 346 | 438 | 608 | 349 | 436 | 505 | 483 | 555 | 429 | 466 | 316 | 439 | 92 |
| 3 | 327 | 397 | 399 | 560 | 329 | 427 | 478 | 418 | 525 | 413 | 460 | 301 | 420 | 78 |
| 3.5 | 281 | 439 | 372 | 480 | 299 | 362 | 418 | 435 | 468 | 366 | 384 | 261 | 380 | 72 |
| 4 | 244 | 325 | 335 | 433 | 269 | 346 | 395 | 393 | 457 | 322 | 396 | 242 | 346 | 71 |
| 6 | 179 | 208 | 222 | 275 | 186 | 214 | 255 | 251 | 265 | 228 | 224 | 174 | 223 | 33 |
| 8 | 123 | 169 | 159 | 163 | 144 | 148 | 194 | 159 | 189 | 155 | 151 | 117 | 156 | 23 |
| 12 | 72.4 | 107 | 103 | 106 | 87.5 | 95.3 | 123 | 99.4 | 110 | 83.6 | 92.0 | 81.8 | 96.3 | 14.54 |
| 14 | 62.4 | 91.5 | 91.0 | 94.6 | 77.6 | 79.4 | 89.6 | 82.9 | 82.8 | 66.9 | 74.3 | 65.4 | 79.9 | 10.9 |
| 24 | 23.3 | 33.2 | 31.2 | 32.2 | 28.8 | 25.3 | 33.5 | 24.2 | 26.3 | 21.0 | 28.9 | 23.9 | 29.7 | 4.3 | unit: ng/mL
*: below sensitivity

TABLE 4B

Mean Plasma Concentration - Time Profile of Ketorolac Tromethamine
Tablets Described in Example 7 (Treatment B)

| Time (hr) | 1-B | 2-B | 3-B | 4-B | 5-B | 6-B | 7-B | 8-B | 9-B | 10-B | 11-B | 12-B | Mean | SD |
|---|---|---|---|---|---|---|---|---|---|---|---|---|---|---|
| 0 | 0 | 0 | 0 | 0 | 0 | 0 | 0 | 0 | 0 | 0 | 0 | 0 | 0 | 0 |
| 0.167 | * | * | * | * | * | * | * | * | * | * | * | * | 0 | 0 |
| 0.33 | * | * | * | * | * | * | * | * | * | * | * | * | 0 | 0 |
| 0.5 | * | * | * | * | * | * | * | * | * | 10.8 | * | * | 10.8 | 0.0 |
| 0.67 | * | * | * | * | * | * | * | * | * | 12.5 | * | * | 12.5 | 0.0 |
| 0.83 | * | * | * | 17.2 | * | * | * | * | 15.1 | 13.9 | * | 38.6 | 21.2 | 11.7 |
| 1 | * | * | * | 61.2 | * | 11.3 | 63.1 | * | 27.5 | 15.6 | * | 79.7 | 43.1 | 28.6 |
| 1.33 | * | * | * | 501 | * | 252 | 1045 | 99.5 | 105 | 30.4 | * | 164 | 31.4 | 357 |
| 1.67 | 20.6 | * | * | 811 | * | 960 | 967 | 572 | 552 | 24.3 | * | 308 | 527 | 382 |
| 2 | 37.3 | * | * | 831 | 67.5 | 918 | 766 | 832 | 1015 | 52.0 | * | 584 | 567 | 403 |
| 2.33 | 29.3 | 32.1 | * | 781 | 363 | 727 | 675 | 773 | 753 | 155 | * | 518 | 481 | 312 |
| 2.67 | 24.5 | 205 | 193 | 671 | 874 | 658 | 594 | 656 | 718 | 369 | * | 449 | 492 | 263 |
| 3 | 38.0 | 189 | 879 | 584 | 838 | 541 | 553 | 603 | 618 | 769 | 27.0 | 411 | 504 | 287 |
| 3.5 | 270 | 303 | 890 | 514 | 631 | 464 | 475 | 527 | 557 | 799 | 260 | 357 | 504 | 199 |
| 4 | 727 | 867 | 657 | 448 | 532 | 429 | 434 | 488 | 478 | 698 | 913 | 338 | 562 | 165 |
| 6 | 272 | 390 | 331 | 272 | 322 | 259 | 265 | 251 | 266 | 322 | 409 | 218 | 298 | 58 |
| 8 | 172 | 277 | 209 | 203 | 197 | 179 | 207 | 162 | 151 | 240 | 237 | 171 | 200 | 37 |
| 12 | 109 | 152 | 128 | 127 | 125 | 105 | 128 | 100 | 92.3 | 130 | 121 | 109 | 119 | 16 |
| 14 | 78.0 | 126 | 108 | 97.2 | 110 | 87.2 | 103 | 73.0 | 69.4 | 98.8 | 96.8 | 93.9 | 84.7 | 16.6 |
| 24 | 20.4 | 41.7 | 28.7 | 33.1 | 39.7 | 25.0 | 32.5 | 25.5 | 16.3 | 28.7 | 32.8 | 36.0 | 30.1 | 7.5 | unit: ng/mL
*: below sensitivity

Conclusion

The results as shown in Tables 2 and 3 demonstrate that the oral dosage forms of ketorolac tromethamine of Example 1–7 had excellent dissolution rates.

As shown in FIG. 1 and Tables 4A and 4B, the pharmacokinetic profile of ketorolac tromethamine tablets of Example 7 was comparable to that of the c commercially available ketorolac tablets.

While the invention has been described by way of examples and in terms of the preferred embodiments, it is to be understood that the invention is not limited to the disclosed embodiments. On the contrary, it is intended to cover various modifications as would be apparent to those skilled in the art. Therefore, the scope of the appended claims should be accorded the broadest interpretation so as to encompass all such modifications.

We claim:

1. A pharmaceutical composition consisting essentially of:
    an inert core, about 25–40% by weight of the total composition;
    a drug layer, about 5–15% by weight of the total composition, wherein said drug layer an effective amount of consisting essentially of ketorolac tromethamine, a binder, and a disintegrant;
    a protecting layer, about 5–15% by weight of the total composition; and
    an enteric coating layer, about 40–55% by weight of the total composition.

2. The pharmaceutical composition according to claim 1, wherein said ketorolac tromethamine is about 1–15% by weight of the total pharmaceutical composition.

3. The pharmaceutical composition according to claim 1, wherein said core comprises material which is at least one selected from the group consisting of sucrose, starch, talc, and microcrystalline cellulose.

4. The pharmaceutical composition according to claim 1, wherein said binder of said drug layer is about 0.1–7% by weight of the total pharmaceutical composition.

5. The pharmaceutical composition according to claim 1, wherein said binder of said drug layer comprises at least one polymer which is selected from the group consisting of hydroxypropyl methylcellulose (HPMC), hydroxypropyl cellulose (HPC), polyvinyl pyrrolidone (PVP) and hydroxy methylcellulose (HMC).

6. The pharmaceutical composition according to claim 1, wherein said binder of said drug layer is PVP K-30.

7. The pharmaceutical composition according to claim 1, wherein said disintegrant of said drug layer is about 3–15% by weight of the total pharmaceutical composition.

8. The pharmaceutical composition according to claim 1, wherein said disintegrant of said drug layer comprises at least one selected from the group consisting of starch and sodium starch glycolate.

9. The pharmaceutical composition according to claim 1, wherein said drug layer further comprises a diluent which is at least one selected from the group consisting of lactose, sucrose, and mannitose.

10. The pharmaceutical composition according to claim 1, wherein said protecting layer comprises at least one polymer which is selected from the group consisting of hydroxypropyl methylcellulose (HPMC), hydroxypropyl cellulose (HPC), and Hydroxymethylcellulose (HMC).

11. The pharmaceutical composition according to claim 1, wherein said protecting layer comprises hydroxypropyl methylcellulose.

12. The pharmaceutical composition according to claim 11, wherein said protecting layer further comprises a plasticizer which is at least one selected from the group consisting of dimethyl phthalate, diethyl phthalate, triacetin, triethyl citrate, and polyethylene glycol (PEG).

13. The pharmaceutical composition according to claim 1, wherein said enteric coating layer comprises at least one polymer which is selected from the group consisting of hydroxypropylmethylcellulose phthalate (HPMCP), cellulose acetate phthalate (CAP), Eudragit L, and Eudragit S; and at least one plasticizer which is selected from the group consisting of dimethyl phthalate, diethyl phthalate, triacetin, triethyl citrate, and polyethylene glycol (PEG).

14. A method for preparing the pharmaceutical composition according to claim 1 comprising:
providing the inert core;
spraying the drug layer onto the core to form a drug-containing core;
spraying the protecting layer onto said drug-containing core to form a protecting layer-containing drug granule;
spraying the enteric coating layer onto said protecting layer-containing drug granule to form the pharmaceutical composition.

15. A method for treating patients with pain comprising orally administering to said patients a therapeutically effective amount of the pharmaceutical composition according to claim 1.

16. A pain-treating agent comprising the pharmaceutical composition according to claim 1.

* * * * *